US012629084B2

(12) United States Patent
Suematsu et al.

(10) Patent No.: US 12,629,084 B2
(45) Date of Patent: May 19, 2026

(54) ELECTROENCEPHALOGRAM SIGNAL PROCESSING APPARATUS AND ELECTROENCEPHALOGRAM SIGNAL PROCESSING SYSTEM

(71) Applicant: NIHON KOHDEN CORPORATION, Tokyo (JP)

(72) Inventors: Kazumi Suematsu, Tokorozawa (JP); Yusuke Kamikura, Tokorozawa (JP); Mari Yamada, Tokorozawa (JP); Ryota Masuda, Tokorozawa (JP)

(73) Assignee: Nihon Kohden Corporation, Tokyo (JP)

( * ) Notice: Subject to any disclaimer, the term of this patent is extended or adjusted under 35 U.S.C. 154(b) by 761 days.

(21) Appl. No.: 17/933,053

(22) Filed: Sep. 16, 2022

(65) Prior Publication Data

US 2023/0100035 A1     Mar. 30, 2023

(30) Foreign Application Priority Data

Sep. 24, 2021     (JP) ................................. 2021-155600

(51) Int. Cl.
*A61B 5/00*         (2006.01)
*A61B 5/291*        (2021.01)
(Continued)

(52) U.S. Cl.
CPC .............. *A61B 5/384* (2021.01); *A61B 5/291* (2021.01); *A61B 5/372* (2021.01); *G06F 3/015* (2013.01)

(58) Field of Classification Search
CPC ......... A61B 5/384; A61B 5/291; A61B 5/372; A61B 5/742; G06F 3/015
See application file for complete search history.

(56) References Cited

U.S. PATENT DOCUMENTS 6,322,516 B1 * 11/2001 Masuda ............... A61B 5/0285
                                                    600/490
11,000,221 B2 * 5/2021 Tahara ................... A61B 5/378
(Continued)

FOREIGN PATENT DOCUMENTS

CN          113040788 A     6/2021
JP       2010233720 A    10/2010
(Continued)

OTHER PUBLICATIONS

Office Action issued in Japanese Patent Application No. 2021-155600, issued Dec. 17, 2024, 5 pages including 3 pages of English translation,.

*Primary Examiner* — May A Abouelela
(74) *Attorney, Agent, or Firm* — Dorsey & Whitney LLP

(57)     ABSTRACT

An electroencephalogram signal processing apparatus includes an interface and one or more processors. The interface receives, from each of a plurality of electrodes attached to a head of a subject, an electroencephalogram signal corresponding to a change over time in a brain activity potential of the subject. The processor obtains a value of an electroencephalogram parameter for each of the plurality of electrodes by processing the electroencephalogram signal, and the processor outputs data for plotting the value on a radar chart. A plurality of regions to each of which at least one electrode is attached are set in the head. Each of a plurality of coordinate axes provided in the radar chart is associated with a corresponding one of the plurality of regions.

14 Claims, 6 Drawing Sheets

(51) Int. Cl.
    *A61B 5/372*         (2021.01)
    *A61B 5/384*         (2021.01)
    *G06F 3/01*          (2006.01)

(56)          References Cited

U.S. PATENT DOCUMENTS

| | | | | |
|---|---|---|---|---|
| 11,507,924 | B1 * | 11/2022 | Kocher | A61B 5/0057 |
| 11,559,237 | B1 * | 1/2023 | Agrawal | A61B 5/7203 |
| 12,251,236 | B2 * | 3/2025 | Aimone | A61B 5/7455 |
| 2011/0130675 | A1 * | 6/2011 | Bibian | A61B 5/372 |
| | | | | 600/544 |
| 2017/0007147 | A1 * | 1/2017 | Hasegawa | A61B 5/162 |
| 2017/0325720 | A1 * | 11/2017 | Hasegawa | A61B 5/117 |
| 2018/0125409 | A1 * | 5/2018 | Tahara | A61B 5/378 |
| 2019/0246927 | A1 * | 8/2019 | Väyrynen | A61B 5/7264 |
| 2019/0247662 | A1 * | 8/2019 | Poltroak | A61N 1/0534 |
| 2020/0069236 | A1 * | 3/2020 | Modarres | A61B 5/374 |
| 2020/0107741 | A1 * | 4/2020 | Fruitwala | A61B 5/291 |
| 2020/0329990 | A1 * | 10/2020 | Laszlo | A61B 5/7257 |
| 2021/0020285 | A1 * | 1/2021 | Hall | G16H 15/00 |
| 2021/0022671 | A1 * | 1/2021 | Lesmy | A61B 5/374 |
| 2021/0052209 | A1 * | 2/2021 | Hecox | G16H 40/63 |
| 2021/0093247 | A1 * | 4/2021 | Pyrzowski | A61B 5/7264 |
| 2021/0259617 | A1 * | 8/2021 | Tanishima | A61B 5/743 |
| 2021/0369181 | A1 * | 12/2021 | Nierenberg | G16H 50/50 |
| 2021/0401355 | A1 * | 12/2021 | Osorio | A61B 5/7267 |
| 2022/0061743 | A1 * | 3/2022 | Christensen | A61B 5/31 |
| 2022/0104751 | A1 * | 4/2022 | Jooris | A61B 5/374 |
| 2022/0160291 | A1 * | 5/2022 | Kadambi | A61B 5/1128 |
| 2022/0369993 | A1 * | 11/2022 | Bolthouse | A61B 5/369 |
| 2023/0055867 | A1 * | 2/2023 | Xu | A61B 5/0006 |
| 2023/0106556 | A1 * | 4/2023 | Lee | G16H 50/30 |
| | | | | 600/544 |
| 2023/0131710 | A1 * | 4/2023 | Tass | A61B 5/742 |
| | | | | 601/46 |
| 2023/0147888 | A1 * | 5/2023 | Toth | G06T 11/206 |
| | | | | 345/440 |
| 2023/0178206 | A1 * | 6/2023 | Pino | G16H 50/30 |
| | | | | 600/545 |
| 2023/0186786 | A1 * | 6/2023 | Zhu | H04R 1/403 |
| 2023/0190185 | A1 * | 6/2023 | Dvorak | A61B 5/165 |
| | | | | 600/544 |
| 2023/0210399 | A1 * | 7/2023 | May | G01R 33/4808 |
| | | | | 600/410 |
| 2023/0293036 | A1 * | 9/2023 | Ogawa | A61B 5/375 |
| | | | | 600/301 |
| 2024/0019932 | A1 * | 1/2024 | Imamura | A61F 2/72 |
| 2024/0156390 | A1 * | 5/2024 | Nierenberg | A61B 5/725 |

FOREIGN PATENT DOCUMENTS

| | | |
|---|---|---|
| JP | 2016221056 A | 12/2016 |
| JP | 2018046899 A | 3/2018 |
| JP | 2018068510 A | 5/2018 |

* cited by examiner

● Current status

⦸ X hours ago

○ Y hours ago

ELECTROENCEPHALOGRAM SIGNAL PROCESSING APPARATUS AND ELECTROENCEPHALOGRAM SIGNAL PROCESSING SYSTEM

CROSS-REFERENCE TO RELATED APPLICATIONS

This application is based on and claims priority under 35 USC 119 from Japanese Patent Application No. 2021-155600 filed on Sep. 24, 2021, the contents of which are incorporated herein by reference.

TECHNICAL FIELD

The presently disclosed subject matter relates to an electroencephalogram signal processing system that quantifies and visualizes a brain activity state of a subject regarding a plurality of features. The presently disclosed subject matter also relates to an electroencephalogram signal processing apparatus provided in the system and a computer program executable by a processor mounted on the apparatus.

BACKGROUND ART

Patent Literature 1 discloses a technique of quantifying a brain activity state of a subject regarding a plurality of features and visualizing the brain activity state using an orthogonal coordinate system including a plurality of coordinate axes corresponding to the plurality of features.

CITATION LIST

Patent Literature

Patent Literature 1: JP2018-046899A

SUMMARY

An object of the presently disclosed subject matter is to provide a novel method for visualizing a brain activity state of a subject.

A first aspect for achieving the above object provides an electroencephalogram signal processing apparatus including:

an interface configured to receive, from each of a plurality of electrodes attached to a head of a subject, an electroencephalogram signal corresponding to a change over time in a brain activity potential of the subject; and one or more processors configured to:

obtain a value of an electroencephalogram parameter for each of the plurality of electrodes by processing the electroencephalogram signal: and output data for platting the value on a radar chart.

A plurality of regions to each of which at least one electrode is attached are set in the head. Each of a plurality of coordinate axes provided in the radar chart is associated with a corresponding one of the plurality of regions.

A second aspect of the presently disclosed subject matter provides a non-transitory computer-readable medium stores a computer program executable by one or more processors mounted on an electroencephalogram signal processing apparatus.

The electroencephalogram signal processing apparatus executes:

receiving, from each of a plurality of electrodes attached to a head of a subject, an electroencephalogram signal corresponding to a change over time in a brain activity potential of the subject;

obtaining a value of an electroencephalogram parameter for each of the plurality of electrodes by processing the electroencephalogram signal; and outputting data for plotting the value of the electroencephalogram parameter on a radar chart.

A plurality of regions to each of which at least one electrode is attached are set in the head.

Each of a plurality of coordinate axes provided in the radar chart is associated with a corresponding one of the plurality of regions.

A third aspect for achieving the above object provides an electroencephalogram signal processing system includes:

a plurality of electrodes configured to be attached to a head of a subject;

a signal processing apparatus configured to obtain a value of an electroencephalogram parameter for each of the plurality of electrodes by processing an electroencephalogram signal corresponding to a change over time in a brain activity potential of the subject output from each of the plurality of electrodes and a visualization apparatus configured to visualize a radar chart in which the value of the electroencephalogram parameter is plotted.

A plurality of regions to each of which at least one electrode is attached are set in the head.

Each of a plurality of coordinate axes provided in the radar chart is associated with a corresponding one of the plurality of regions.

According to the configurations according to the above aspects, it is possible to provide a novel method for visualizing a brain activity state, in which a relative relationship among values of electroencephalogram parameters obtained for a plurality of regions set for the head of the subject is illustrated in the radar chart. That is, a user can research the brain activity state of the subject that can be read from the radar chart in association with information on positions in the brain.

DESCRIPTION OF EMBODIMENTS

An example of an embodiment will be described in detail below with reference to the accompanying drawings.

Figure 1:
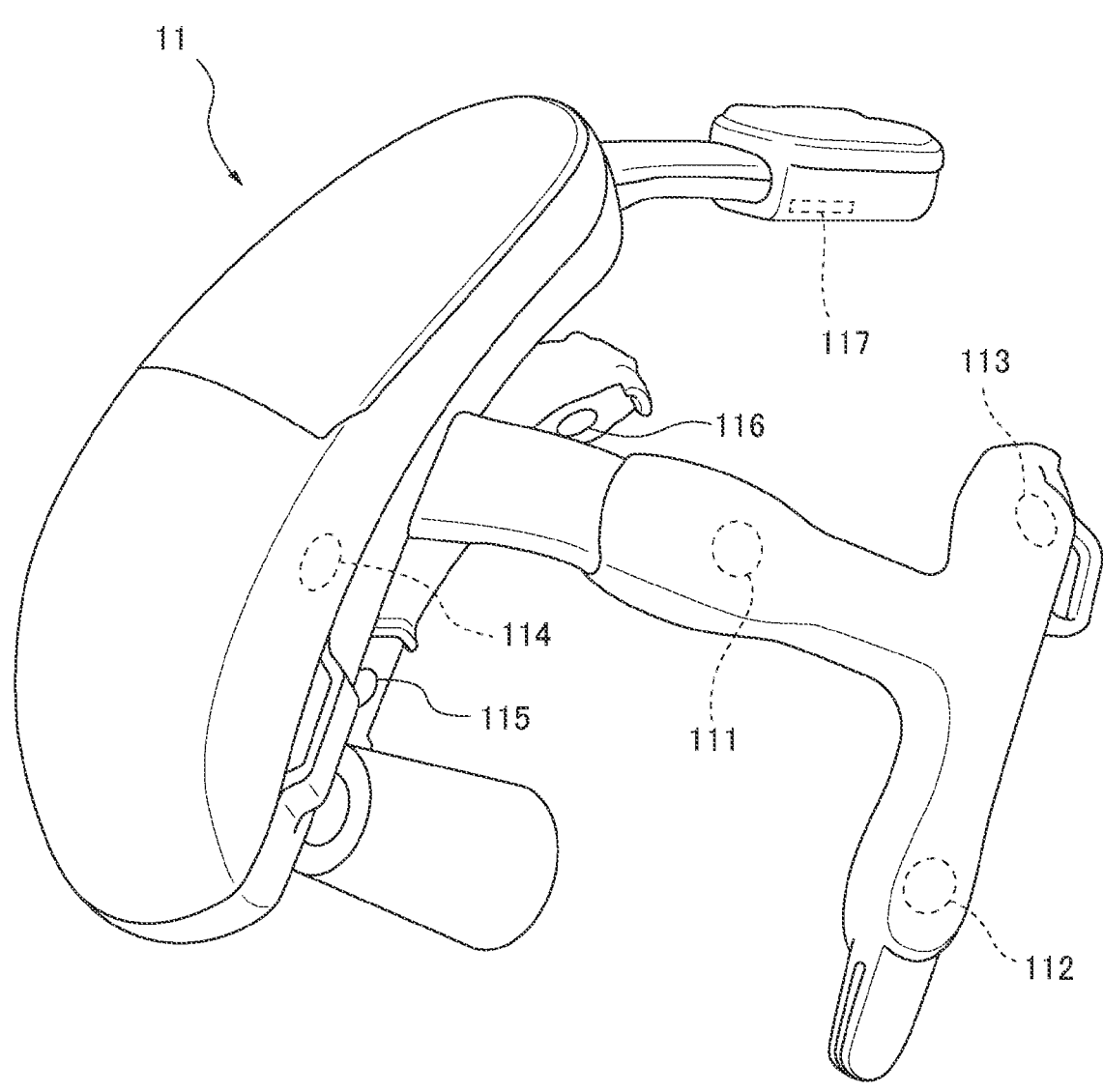
FIG. 1 illustrates an appearance of a headset provided in an electroencephalogram signal processing system according to an embodiment.

FIG. 1 illustrates an appearance of a headset 11 provided in an electroencephalogram signal processing system 10 (hereinafter abbreviated as signal processing system 10) according to the embodiment. The headset 11 includes a first electrode 111, a second electrode 112, a third electrode 113, a fourth electrode 114, a fifth electrode 115, a sixth electrode 116, and a seventh electrode 117. In the following description, the first electrode 111, the second electrode 112, the third electrode 113, the fourth electrode 114, the fifth electrode 115, the sixth electrode 116, and the seventh electrode 117 are collectively referred to as "a plurality of electrodes 110" as necessary.

The headset 11 is worn on a head of a subject. The first electrode 111, the second electrode 112, and the third electrode 113 are supported on a left head of the subject when the headset 11 is worn. The fourth electrode 114, the fifth electrode 115, and the sixth electrode 116 are supported on a right head of the subject when the headset 11 is worn. The seventh electrode 117 is supported on a top of the head of the subject when the headset 11 is worn.

Figure 2:
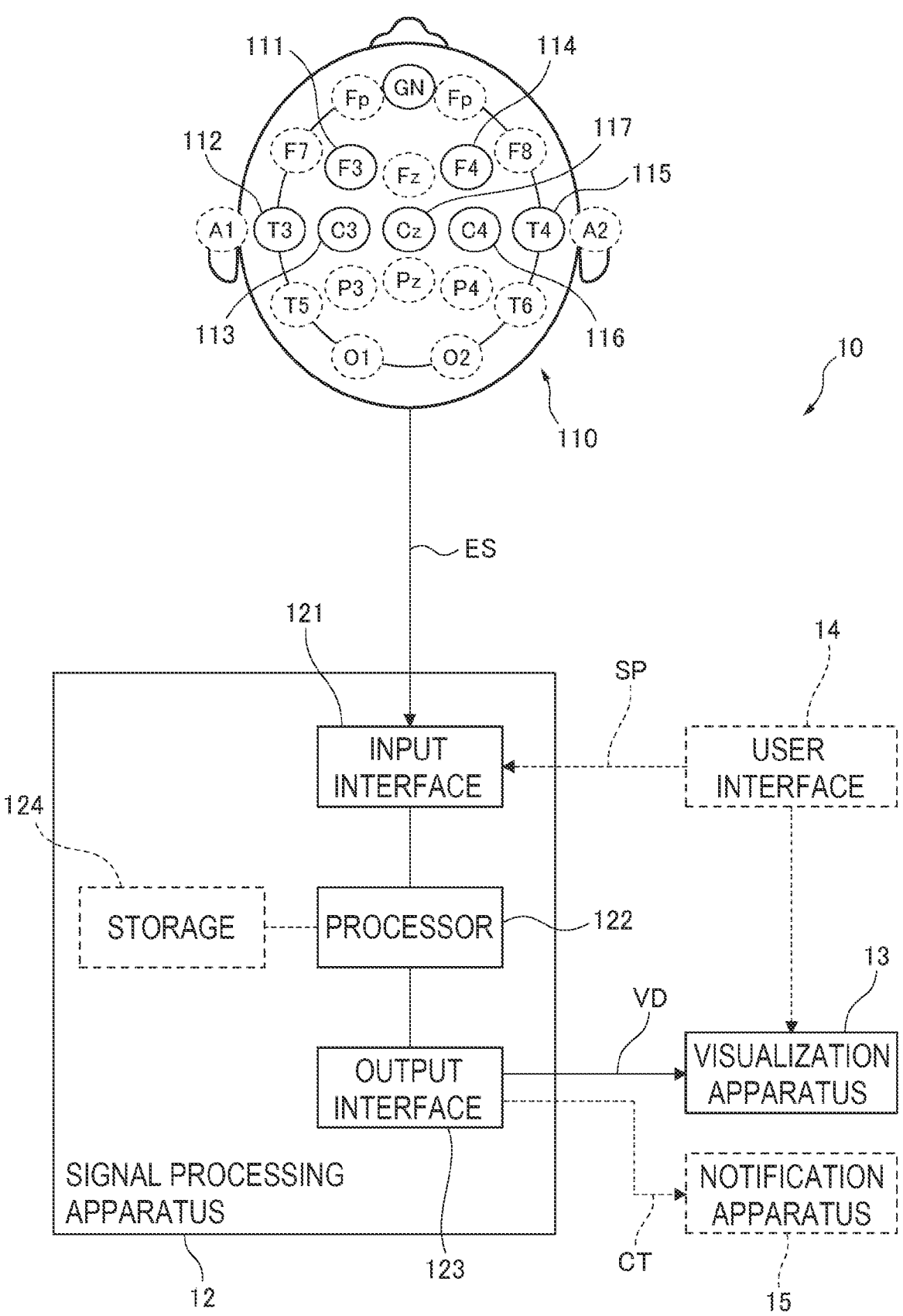
FIG. 2 illustrates a functional configuration of the electroencephalogram signal processing system according to the embodiment.

As illustrated in FIG. 2, the first electrode 111, the second electrode 112, and the third electrode 113 are set respectively in the F3 electrode position, the T3 electrode position, and the C3 electrode position in the 10-20 method. The fourth electrode 114, the fifth electrode 115, and the sixth electrode 116 are set respectively in the F4 electrode position, the T4 electrode position, and the C4 electrode position in the 10-20 method. The seventh electrode 117 is set in the Cz electrode position in the 10-20 method.

Each of the plurality of electrodes 110 detects an activity potential in a corresponding position of the brain of the subject through a scalp, a skull, a spinal fluid, a hard membrane, or the like that faces the electrode. When the brain activity potential is detected continuously over time, the electrode outputs an electroencephalogram signal ES corresponding to a change over time in the brain activity potential. The electroencephalogram signal ES may be an analog signal or a digital signal.

The signal processing system 10 includes an electroencephalogram signal processing apparatus 12 (hereinafter abbreviated as signal processing apparatus 12). The signal processing apparatus 12 may be provided in the headset 11 illustrated in FIG. 1, or be provided as an apparatus independent of the headset 11. In the latter case, the electroencephalogram signal ES is transmitted from the headset 11 to the signal processing apparatus 12 via wired or wireless communication.

The signal processing apparatus 12 includes an input interface 121. The input interface 121 receives the electroencephalogram signal ES output from each of the plurality of electrodes 110, When the electroencephalogram signal ES is an analog signal, the input interface 121 includes an appropriate conversion circuit including an A/D converter.

The signal processing apparatus 12 includes a processor 122. The processor 122 obtains a value of an electroencephalogram parameter for each of the plurality of electrodes 110 by processing the electroencephalogram signal ES.

In the present embodiment, the processor 122 performs a fast Fourier transform on the electroencephalogram signal ES output from each of the plurality of electrodes 110 and obtains total power that is an example of the electroencephalogram parameter. The fast Fourier transform is an example of frequency analysis processing. Examples of other electroencephalogram parameters that may be obtained through the frequency analysis processing include an αδ ratio, an edge frequency, and power in a specific electroencephalogram frequency band. Examples of the specific electroencephalograms include δ waves, θ waves, α waves, β waves, and γ waves.

The signal processing system 10 includes a visualization apparatus 13. The visualization apparatus 13 visualizes a radar chart in which values of a plurality of electroencephalogram parameters obtained by the signal processing apparatus 12 are plotted. The visualization may be performed by displaying the radar chart on a display device such as a display, or by printing the radar chart through a printer or the like.

Figure 3:
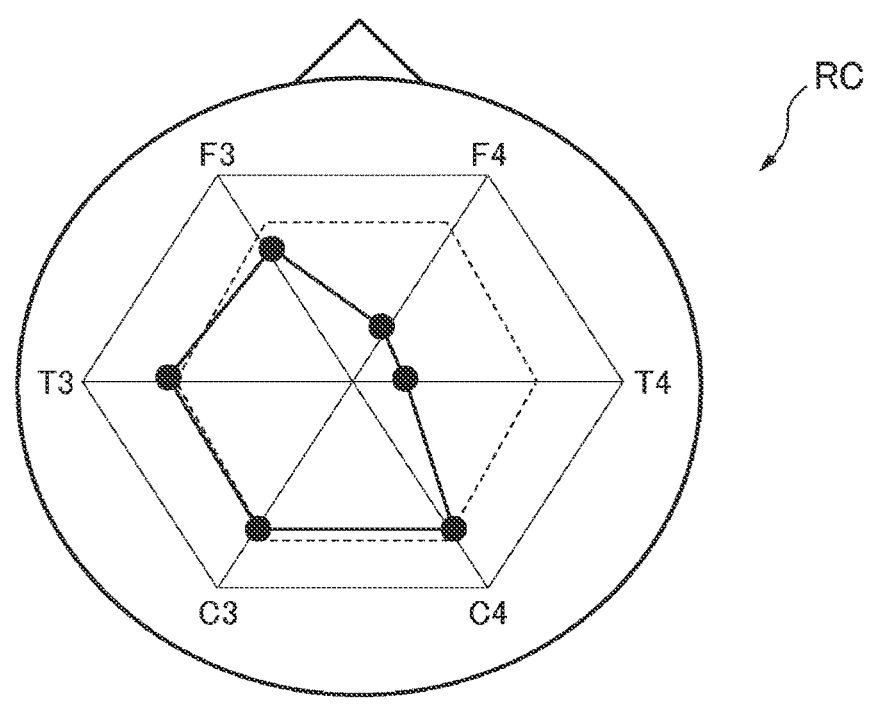
FIG. 3 illustrates an example of a radar chart visualized by a visualization apparatus of FIG. 2.

FIG. 3 illustrates a radar chart RC presented by the visualization apparatus 13. The radar chart RC includes an F3 coordinate axis, a T3 coordinate axis, a C3 coordinate axis, an F4 coordinate axis, a T4 coordinate axis, and a C4 coordinate axis. The F3 coordinate axis, the T3 coordinate axis, the C3 coordinate axis, the F4 coordinate axis, the T4 coordinate axis, and the C4 coordinate axis are respectively associated with the F3 electrode position, the T3 electrode position, the C3 electrode position, the F4 electrode position, the T4 electrode position, and the C4 electrode position described above. The F3 electrode position, the T3 electrode position, the C3 electrode position, the F4 electrode position, the T4 electrode position, and the C4 electrode position are examples of a plurality of regions set for the head of the subject.

A value of total power obtained based on the electroencephalogram signal ES output from the first electrode 111 is plotted on the F3 coordinate axis of the radar chart RC. A value of total power obtained based on the electroencephalogram signal ES output from the second electrode 112 is plotted on the T3 coordinate axis of the radar chart RC. A value of total power obtained based on the electroencephalogram signal ES output from the third electrode 113 is plotted on the C3 coordinate axis of the radar chart RC. A value of total power obtained based on the electroencephalogram signal ES output from the fourth electrode 114 is plotted on the F4 coordinate axis of the radar chart RC. A value of total power obtained based on the electroencephalogram signal ES output from the fifth electrode 115 is plotted on the T4 coordinate axis of the radar chart RC. A value of total power obtained based on the electroencephalogram signal ES output from the sixth electrode 116 is plotted on the C4 coordinate axis of the radar chart RC.

As illustrated in FIG. 2, the signal processing apparatus 12 includes an output interface 123. The processor 122 outputs, from the output interface 123, visualization data VD for providing the above-described radar chart RC to the visualization apparatus 13. The visualization data VD may be provided in a form of analog data or digital data. When the visualization data VD is provided in the form of analog data, the output interface 123 includes an appropriate conversion circuit including a D/A converter. The visualization apparatus 13 visualizes the radar chart RC based on the visualization data VD.

According to the above configuration, it is possible to provide a novel method for visualizing a brain activity state, in which a relative relationship among values of electroencephalogram parameters obtained for a plurality of regions set for the head of the subject is illustrated in a radar chart, That is, a user can research the brain activity state of the subject that can be read from the radar chart in association with information on positions in the brain.

In the present embodiment, the plurality of regions associated with the plurality of coordinate axes provided in the radar chart RC are set to be bilaterally symmetrical regarding the head of the subject. Therefore, the radar chart RC visualized by the visualization apparatus 13 may include information on left-right symmetry of a distribution of obtained electroencephalogram parameter values.

When the brain activity state of the subject is normal, the distribution of the obtained electroencephalogram parameter values generally illustrates symmetry between the left head and the right head. In other words, when the distribution of total power values is asymmetric between the left head and the right head as illustrated in FIG. 3, an abnormality in the brain activity state of the subject is suspected. For example, the asymmetric distribution as illustrated in FIG. 3 is obtained when an ischemic state caused by stroke or the like occurs in the brain. The user can intuitively obtain information on such symmetry through a shape of a figure obtained by connecting a plurality of points plotted on the radar chart RC with a line. Therefore, it is possible to support the determination of the brain activity state of the subject.

The processor 122 of the signal processing apparatus 12 may obtain the electroencephalogram parameter value at a plurality of time points. The electroencephalogram parameter value may be obtained intermittently based on the electroencephalogram signal ES at a time point at which predetermined time elapses, and a statistical value of the electroencephalogram parameter may be obtained each time the predetermined time elapses based on the electroencephalogram signal ES continuously obtained during the predetermined time. Examples of the statistical value include an average value, an intermediate value, and a mode value. The length of the predetermined time is appropriately set according to the brain activity state to be determined. Examples of the unit of the length of the predetermined time include minutes, hours, and days.

In this case, the processor 122 outputs the visualization data VD from the output interface 123 each time the electroencephalogram parameter value is obtained. The visualization data VD causes the visualization apparatus 13 to visualize the radar chart RC.

Figure 4:
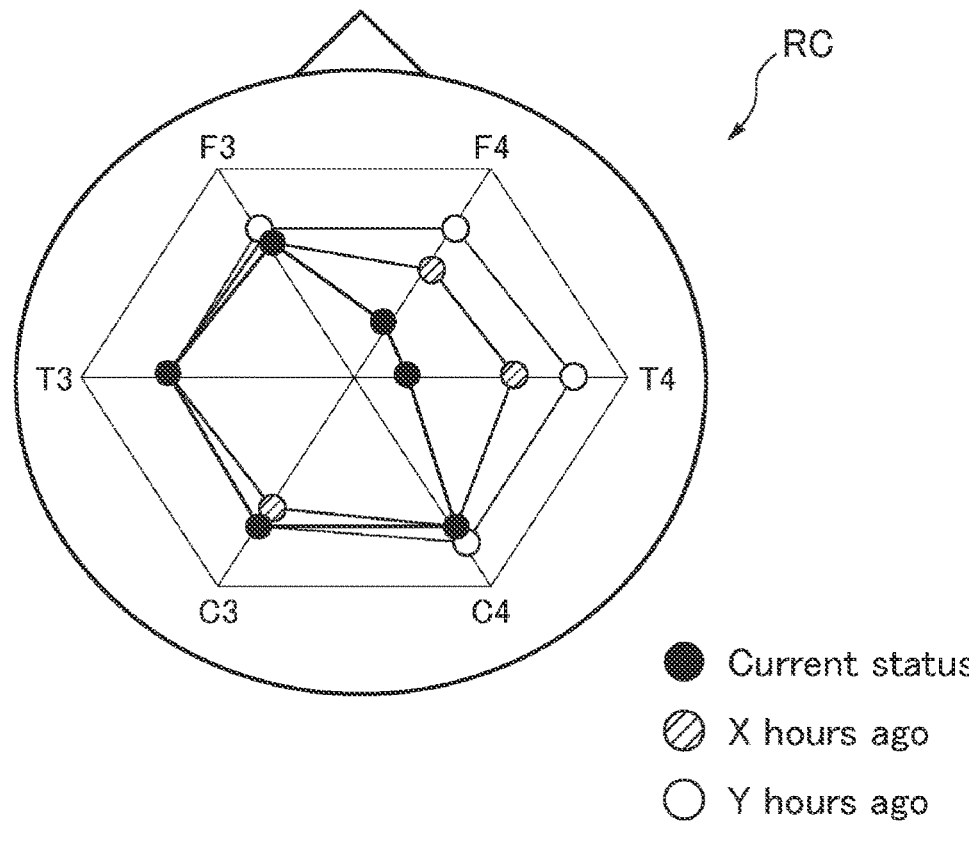
FIG. 4 illustrates another example of the radar chart visualized by the visualization apparatus of FIG. 2.

FIG. 4 illustrates the radar chart RC visualized based on electroencephalogram parameter values obtained at a plurality of time points. Black circles represent electroencephalogram parameter values plotted through a latest obtaining process. Hatched circles represent electroencephalogram parameter values plotted through a previous obtaining process. White circles represent electroencephalogram parameter values plotted through a further previous obtaining process.

According to such a configuration, a change over time in the electroencephalogram parameter values can be visualized on the radar chart RC, The user may be able to obtain findings of the brain activity state of the subject based on the change over time.

Figure 5:
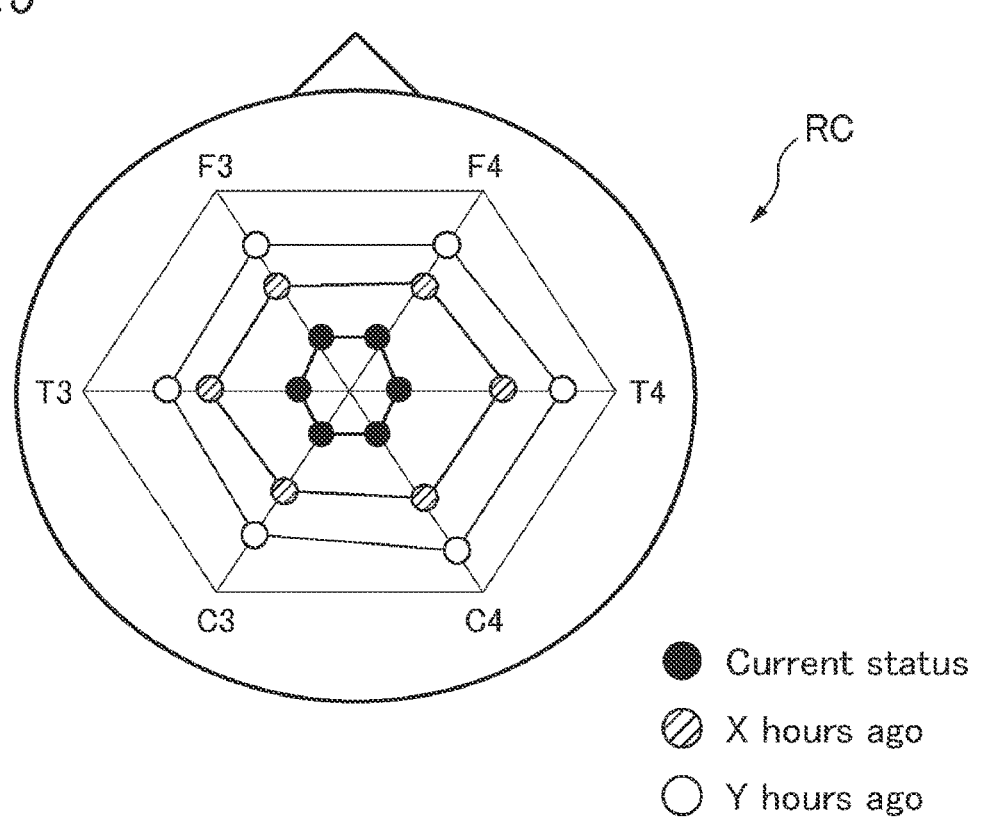
FIG. 5 illustrates another example of the radar chart visualized by the visualization apparatus of FIG. 2.

For example, the radar chart RC of FIG. 5 illustrates a change over time in which total power values decrease while maintaining the distribution of substantially left-right symmetry. Such a change can be considered as a sign (for example, brain death state) in which the brain activity is entirely deteriorated. Therefore, by referring to the change over time of the electroencephalogram parameter values, it is possible to support the determination of the abnormality of the brain activity state that cannot be determined simply by information indicating whether the distribution of electroencephalogram parameter values is symmetrical between the left head and the right head.

Figure 6:
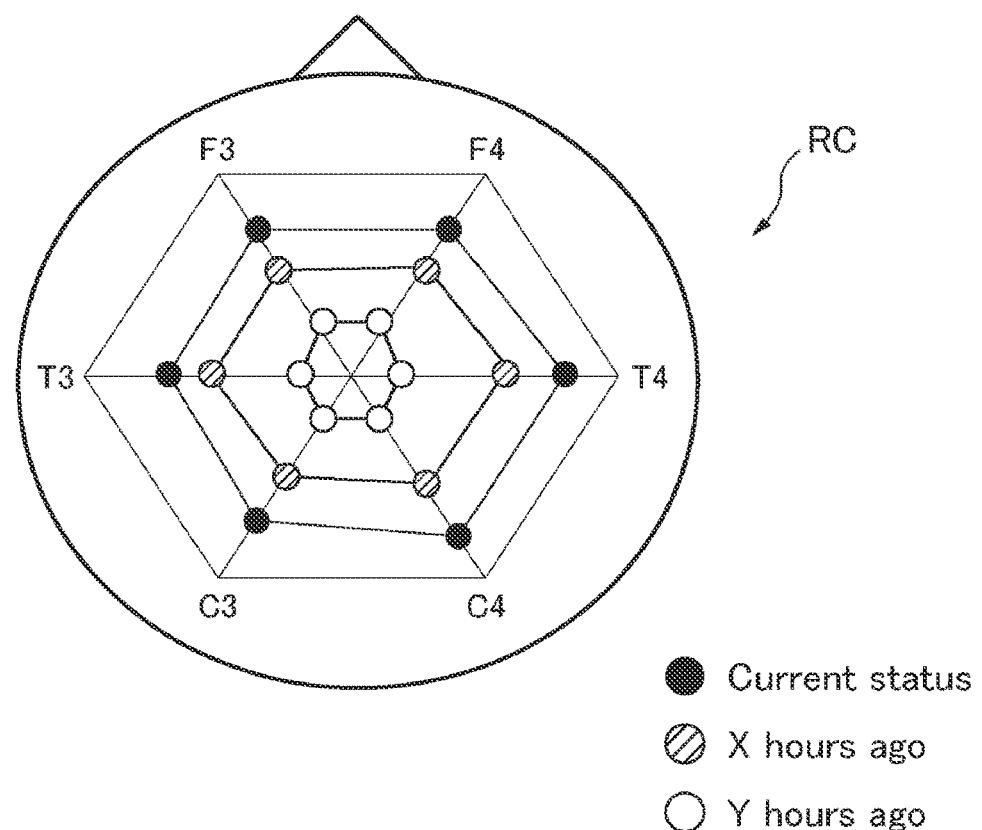
FIG. 6 illustrates another example of the radar chart visualized by the visualization apparatus of FIG. 2.

On the other hand, the radar chart RC of FIG. 6 illustrates a change over time in which total power values increase while maintaining the distribution of substantially left-right symmetry. From such a change, a recovery tendency of a brain function of the subject can be read.

In the examples illustrated in FIGS. 4 to 6, electroencephalogram parameter values obtained at a time point closer to a current time point are displayed in a more emphasized manner. The emphasis may be performed by making the color, the thickness of the line, the type of the line, the shading, and the like different from each other.

According to such a configuration, it is possible to cause the user to more intuitively grasp the change over time of the electroencephalogram parameter values, and it is possible to improve the capability of supporting the determination of the abnormality of the brain activity state.

Figure 7A:
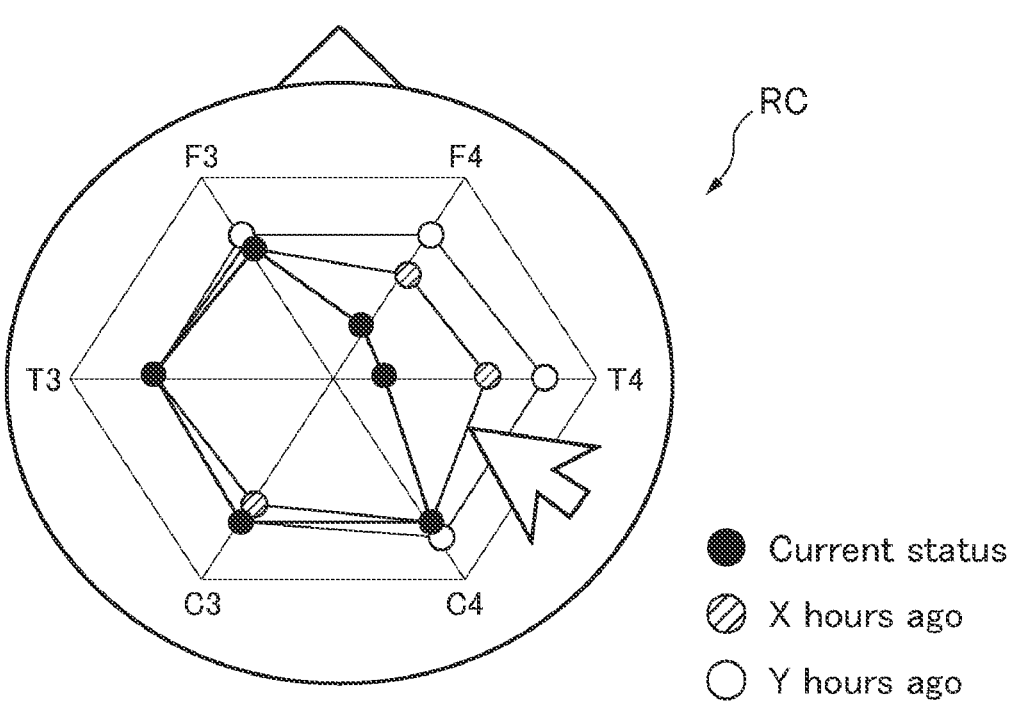
FIGS. 7A and 7B illustrate another example of the radar chart visualized by the visualization apparatus of FIG. 2.
Figure 7B:
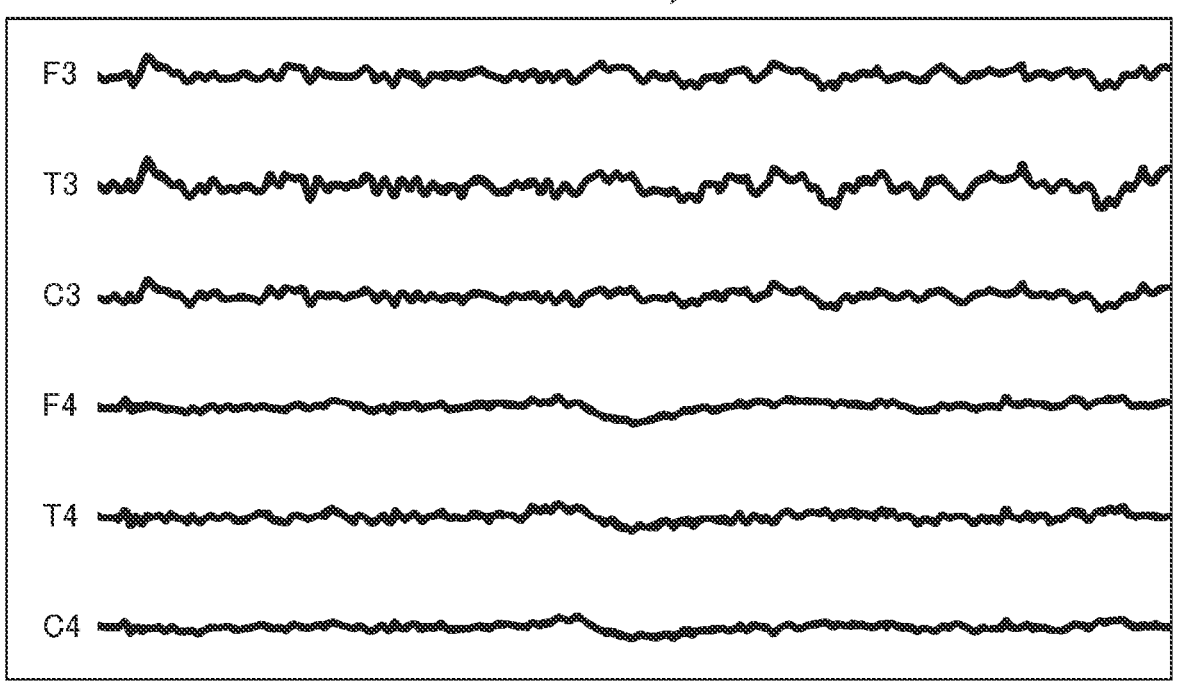

As illustrated in FIGS. 7A and 7B, in the visualization apparatus 13, a plot related to an electroencephalogram parameter value obtained at a specific time point in the radar chart RC may be specified. In this case, the visualization apparatus 13 may visualize the electroencephalogram signal ES obtained at the specified time point. A region including the electroencephalogram parameter value obtained at the specific time point in the radar chart RC is an example of a specific region in the radar chart.

Specifically, as illustrated in FIG. 2, the signal processing system 10 may include a user interface 14. The user interface 14 may have an appropriate configuration for supporting specification of a plot related to an electroencephalogram parameter value obtained at a specific time point in the radar chart RC visualized by the visualization apparatus 13. The user interface 14 may be implemented by a mouse, a pointer, a touch panel constituting a part of the visualization apparatus 13, and the like.

When the plot related to the electroencephalogram parameter value obtained at the specific time point in the radar chart RC is specified, specification information SP indicating at which time point the plot related to the obtained electroencephalogram parameter value is specified is transmitted from the user interface 14 to the signal processing apparatus 12.

Each time the electroencephalogram parameter values are obtained, the signal processing apparatus 12 stores, in a storage 124, data corresponding to the electroencephalogram signal ES used in this process. The processor 122 reads, from the storage 124, data corresponding to the electroencephalogram signal ES used in the electroencephalogram parameter value obtaining process performed at the time point specified by the specification information SP received by the input interface 121, and outputs, from the output interface 123, the visualization data VD that causes the visualization apparatus 13 to visualize the electroencephalogram signal ES. The visualization apparatus 13 visualizes the electroencephalogram signal ES based on the visualization data VD as illustrated in FIGS. 7A and 7B.

According to such a configuration, when the user is doubtful about or interested in information visualized as the radar chart RC, it is possible to immediately check electroencephalograms that are sources of the information. Accordingly, it is possible to improve the capability of supporting the determination of the abnormality of the brain activity state.

The above configuration is also applicable to the radar chart RC in FIG. 3 in which only electroencephalogram parameter values related to a single time point are visualized.

Figure 8A:
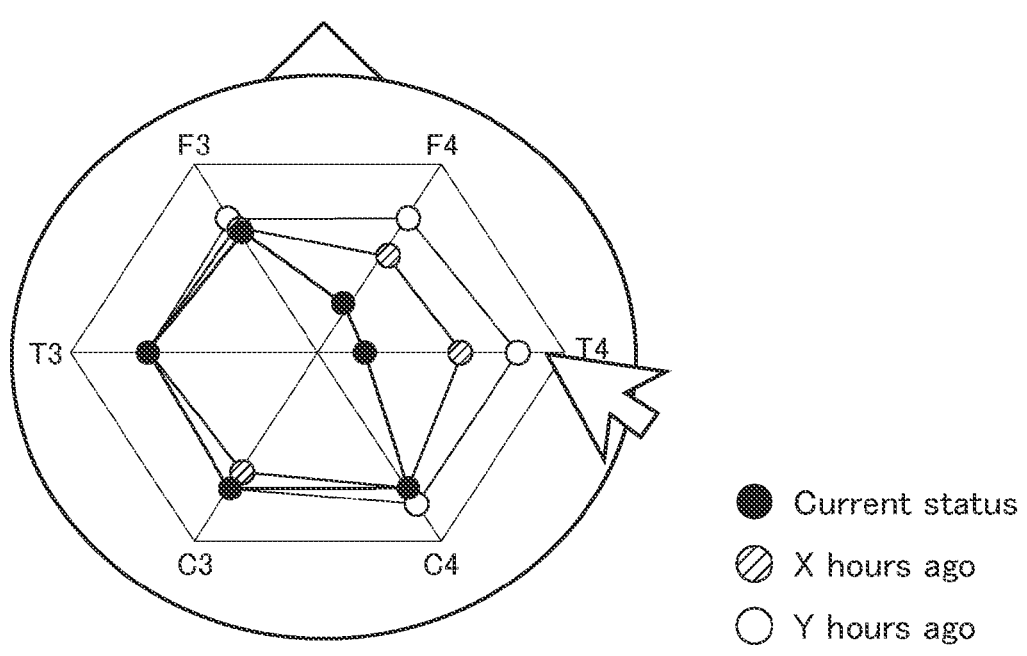
FIGS. 8A and 8B illustrate another example of the radar chart visualized by the visualization apparatus of FIG. 2.
Figure 8B:
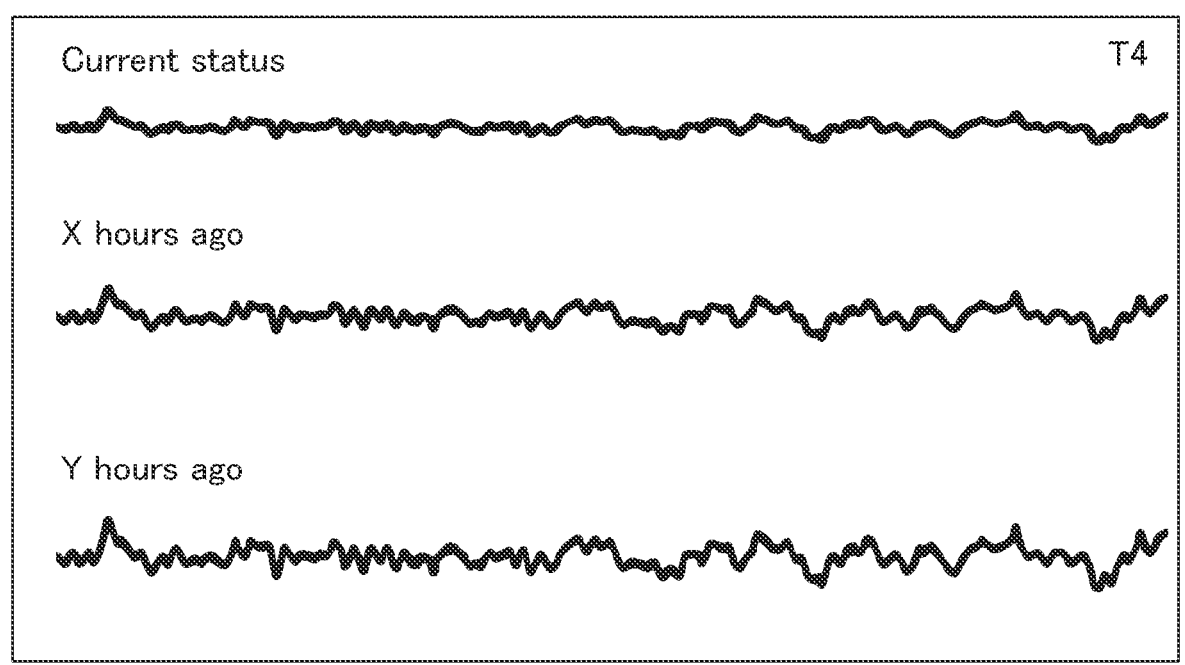

As illustrated in FIGS. 8A and 8B, in the visualization apparatus 13, a specific coordinate axis in the radar chart RC may be specified. In this case, the visualization apparatus 13 may visualize the electroencephalogram signal ES obtained through the electrode corresponding to the specified coordinate axis. The specific coordinate axis in the radar chart RC is an example of a specific region in the radar chart. A plurality of coordinate axes may be specified.

In this case, when the specific coordinate axis in the radar chart RC is specified, the specification information SP indicating which coordinate axis is specified is transmitted from the user interface 14 to the signal processing apparatus 12.

The processor 122 reads, from the storage 124, data corresponding to the electroencephalogram signal ES obtained through the electrode corresponding to the coordinate axis specified by the specification information SP received by the input interface 121, and outputs, from the output interface 123, the visualization data VD that causes the visualization apparatus 13 to visualize the electroencephalogram signal ES. The visualization apparatus 13 visualizes the electroencephalogram signal ES based on the visualization data. VD as illustrated in FIGS. 8A and 8B.

Also with such a configuration, when the user is doubtful about or interested in the information visualized as the radar chart RC, it is possible to immediately check electroencephalograms that are sources of the information. Accordingly, it is possible to improve the capability of supporting the determination of the abnormality of the brain activity state.

In the example illustrated in FIGS. 8A and 8B, a plurality of electroencephalogram signals ES obtained at different time points are arranged in an upper-lower direction. However, the plurality of electroencephalogram signals ES may be displayed in a superimposed manner to share a time axis extending in a left-right direction, and the display mode (type of line, shading of line, color of line, thickness of line, and the like) may be different between the electroencephalogram signals ES so that the plurality of electroencephalogram signals ES obtained at different time points can be distinguished from each other.

The user interface 14 may be able to specify a freely selected region in the radar chart RC. For example, a freely selected region in the radar chart RC may be surrounded by an operation of a cursor by a mouse or a touch operation on a touch panel.

In this case, the specification information SP includes information indicating which region in the radar chart RC is specified. The processor 122 reads, from the storage 124, data corresponding to the electroencephalogram signal ES that is a source of electroencephalogram parameter values provided in the region specified by the specification information SP, and outputs, from the output interface 123, the visualization data VD that causes the visualization apparatus 13 to visualize the electroencephalogram signal ES. The visualization apparatus 13 visualizes the electroencephalogram signal ES based on the visualization data VD.

Reference values corresponding to electroencephalogram parameter values obtained based on the electroencephalogram signal ES of a healthy person may be stored in the storage 124. Examples of the reference values include electroencephalogram parameter values obtained in advance when a brain activity of a subject to be compared is normal, average values of electroencephalogram parameter values obtained in advance for a plurality of healthy subjects, and electroencephalogram parameter values that can be obtained from a healthy subject generally known in literature and the like.

In this case, as illustrated by a broken line in FIG. 3, the reference values may be plotted on the radar chart RC. Specifically, the processor 122 reads the reference values from the storage 124, and outputs from the output interface 123 the visualization data VD that causes the visualization apparatus 13 to visualize the reference values.

According to such a configuration, the obtained electroencephalogram parameter values of the subject can be compared with electroencephalogram parameter values that would be obtained when the brain activity state of the subject is normal. Accordingly, it is possible to improve the capability of supporting the determination of the abnormality of the brain activity state of the subject.

As illustrated in FIG. 2, the signal processing system 10 may include a notification apparatus 15. The notification apparatus 15 may notify the user that at least one of a plurality of electroencephalogram parameter values visualized on the radar chart RC is not normal. The notification can be performed through at least one of a visual notification, an auditory notification, and a tactile notification.

As an example, the notification may be performed when at least one of a plurality of electroencephalogram parameter values is out of a predetermined threshold range. As another example, the notification may be performed when the variation in at least one of a plurality of electroencephalogram parameter values due to a change over time exceeds a threshold value.

The notification may be performed when a statistical value obtained based on a plurality of electroencephalogram parameter values is out of a predetermined threshold range. Examples of the statistical value include a total value, an average value, a maximum value, and a minimum value of a plurality of parameter values. The notification may be performed when a difference between a statistical value of a plurality of parameter values obtained for the left head and a statistical value of a plurality of parameter values obtained for the right head exceeds a threshold.

Specifically, the processor 122 of the signal processing apparatus 12 determines whether a predetermined abnormality condition is satisfied each time an electroencephalogram parameter value is obtained. When determining that at least one electroencephalogram parameter value or a statistical value based on a plurality of brain parameter values satisfies the predetermined abnormality condition, the processor 122 outputs from the output interface 123 a control signal CT that causes the notification apparatus 15 to perform a predetermined notification. The notification apparatus 15 performs notification based on the control signal CT.

According to such a configuration, when the brain activity of the subject deviates from a normal state or is deviating from the normal state, it is possible to prompt the user to respond quickly.

The processor 122 of the signal processing apparatus 12 having the various functions described above may be implemented by a general-purpose microprocessor that operates in cooperation with a general-purpose memory. Examples of the general-purpose microprocessor include a CPU, an MPU, and a GPU. Examples of the general-purpose memory include a ROM and a RAM. In this case, the ROM may store a computer program that executes the above-described processing. The ROM is an example of a non-transitory computer-readable medium storing the computer program. The general-purpose microprocessor specifies at least a part of programs stored in the ROM, loads the program into a RAM, and executes the above-described processing in cooperation with the RAM. The computer program may be pre-installed in the general-purpose memory, or may be downloaded from an external server via a communication network and be installed in the general-purpose memory. In this case, the external server is an example of a non-transitory computer-readable medium storing the computer program. The storage 124 may be implemented by the general-purpose memory.

The processor 122 of the signal processing apparatus 12 having the various functions described above may be implemented by a dedicated integrated circuit that can execute the computer program described above, such as a microcontroller, an ASIC, or an FPGA. In this case, the above computer program is pre-installed in a storage element provided in the dedicated integrated circuit. The storage element is an example of a computer-readable medium storing the computer program. The storage 124 may be implemented by the storage element.

The processor 122 of the signal processing apparatus 12 having the various functions described above may be implemented by a combination of a general-purpose microprocessor and a dedicated integrated circuit.

The above embodiment is merely an example for facilitating understanding of the presently disclosed subject matter. Configurations according to the above embodiment can be appropriately changed and improved without departing from the gist of the presently disclosed subject matter.

In the above embodiment, six regions are set for the head of the subject, and the radar chart RC includes six coordinate axes. However, the number of regions may be changed appropriately as long as the radar chart RC can be created. For example, at least two of a plurality of electrode positions according to the 10-20 method illustrated in FIG. 2 may be appropriately selected.

In the above embodiment, one electrode is associated with one of the plurality of regions set for the head of the subject. However, the number of electrodes associated with each region may be two or more. In this case, an electroencephalogram parameter value provided for visualization on the radar chart RC in each region may be a statistical value based on a plurality of electroencephalogram parameter values obtained through a plurality of electrodes. Examples of the statistical value include an average value, a maximum value, a minimum value, an intermediate value, and a mode value.

In the above embodiment, the processor 122 of the signal processing apparatus 12 obtains electroencephalogram parameter values based on frequency analysis processing. However, electroencephalogram parameter values that can be obtained without the frequency analysis process may be used for visualization on the radar chart RC. Examples of such electroencephalogram parameters include electroencephalogram amplitude, burst suppression, anesthesia depth, sedative level, and artifact.

The signal processing apparatus 12 and the visualization apparatus 13 may be one single apparatus. For example, the above-described visualization method may be implemented by providing another patient monitor that obtains and displays vital parameters (blood pressure, body temperature, respiration, and the like) with the function of the signal processing apparatus 12 and the function of the visualization apparatus 13. Same or similarly, the signal processing apparatus 12, the visualization apparatus 13, and the notification apparatus 15 may be one single apparatus.

The expression at least one of two main bodies A and B" used in the present specification for A and B includes a case where A alone is specified, a case where B alone is specified, and a case where both A and B are specified. Each of the main bodies A and B may be singular or plural unless otherwise specified.

The expression "at least one of three main bodies A, B, and C" used in the present specification for A, B, and C includes a case where A alone is specified, a case where B alone is specified, a case where C alone is specified, a case where A and B are specified, a case where B and C are specified, a case where A and C are specified, and a case where all of A, B, and C are specified. Each of the main bodies A, B, and C may be singular or plural unless otherwise specified. The same applies to a case where four or more bodies are described.

The invention claimed is:

1. An electroencephalogram signal processing apparatus comprising:
   an interface configured to receive, from each of a plurality of electrodes configured to be attached to a head of a subject, an electroencephalogram signal corresponding to a change over time in a brain activity potential of the subject; and
   one or more processors configured to:
      obtain a value of an electroencephalogram parameter for each of the plurality of electrodes by processing the electroencephalogram signal; and
      output data for plotting the value on a radar chart,
   wherein a plurality of regions to each of which at least one electrode is attached are set in the head,
   wherein each of a plurality of coordinate axes provided in the radar chart is associated with a corresponding one of the plurality of regions, and
   wherein the plurality of coordinate axes provided in the radar chart are bilaterally symmetrical regarding the head of the subject, and
   wherein the plotted value in the radar chart provides visualization of the brain activity of the subject in the corresponding one of the plurality of regions.

2. The electroencephalogram signal processing apparatus according to claim 1,
   wherein the plurality of regions are set symmetrically regarding the head.

3. The electroencephalogram signal processing apparatus according to claim 1,
   wherein the processor is configured to:
      obtain the value of the electroencephalogram parameter at a plurality of time points; and
      output data for plotting a change over time in the value on the radar chart.

4. The electroencephalogram signal processing apparatus according to claim 3,
   wherein the processor is configured to output data for plotting the value of the electroencephalogram parameter obtained at a time point closer to a current time point on the radar chart in a more emphasized manner by altering at least one of the output data's color, line thickness, line type, or shading.

5. The electroencephalogram signal processing apparatus according to claim 1, further comprising:
   a storage configured to store data corresponding to the electroencephalogram signal,
   wherein the processor is configured to:
      read from the storage, when specification information specifying a specific region in the radar chart is received by the interface, data corresponding to the electroencephalogram signal used to obtain the value of the electroencephalogram parameter provided in the specific region; and
      output data for visualizing the electroencephalogram signal.

6. The electroencephalogram signal processing apparatus according to claim 5, wherein the specific region corresponds to a specific time point at which the value of the electroencephalogram parameter is obtained.

7. The electroencephalogram signal processing apparatus according to claim 5, wherein the specific region corresponds to at least one of the plurality of regions set for the head.

8. The electroencephalogram signal processing apparatus according to claim 1, further comprising:

a storage configured to store a reference value corresponding to the value of the electroencephalogram parameter obtained based on the electroencephalogram signal of a healthy object, wherein the processor is configured to output data for plotting the reference value on the radar chart.

9. The electroencephalogram signal processing apparatus according to claim 1, wherein the processor is configured to output a control signal that causes a notification apparatus to notify that the plurality of electroencephalogram parameter values are not normal.

10. The electroencephalogram signal processing apparatus according to claim 9, wherein the processor is further configured to determine that the plurality of electroencephalogram parameter values are not normal based on a comparison with a predetermined threshold range.

11. The electroencephalogram signal processing apparatus according to claim 9, wherein the processor is further configured to determine that the plurality of electroencephalogram parameter values are not normal based on a difference between a statistical value of a plurality of parameter values obtained for the left head side and a statistical value of a plurality of parameter values obtained for the right head side exceeds a threshold.

12. The electroencephalogram signal processing apparatus according to claim 1, wherein the processor is configured to obtain the value of the electroencephalogram parameter by performing frequency analysis processing on the electroencephalogram signal.

13. A non-transitory computer-readable medium configured to store a computer program executable by one or more processors mounted on an electroencephalogram signal processing apparatus, wherein the electroencephalogram signal processing apparatus executes:

receiving, from each of a plurality of electrodes configured to be attached to a head of a subject, an electroencephalogram signal corresponding to a change over time in a brain activity potential of the subject;

obtaining a value of an electroencephalogram parameter for each of the plurality of electrodes by processing the electroencephalogram signal; and outputting data for plotting the value of the electroencephalogram parameter on a radar chart, wherein a plurality of regions to each of which at least one electrode is attached are set in the head, wherein each of a plurality of coordinate axes provided in the radar chart is associated with a corresponding one of the plurality of regions, wherein the plurality of coordinate axes provided in the radar chart are bilaterally symmetrical regarding the head of the subject, and wherein the plotted value in the radar chart provides visualization of the brain activity of the subject in the corresponding one of the plurality of regions.

14. An electroencephalogram signal processing system comprising:

a plurality of electrodes configured to be attached to a head of a subject;

a signal processing apparatus configured to obtain a value of an electroencephalogram parameter for each of the plurality of electrodes by processing an electroencephalogram signal corresponding to a change over time in a brain activity potential of the subject output from each of the plurality of electrodes; and a visualization apparatus configured to visualize a radar chart in which the value of the electroencephalogram parameter is plotted, wherein a plurality of regions to each of which at least one electrode is attached are set in the head, wherein each of a plurality of coordinate axes provided in the radar chart is associated with a corresponding one of the plurality of regions wherein the plurality of coordinate axes provided in the radar chart are bilaterally symmetrical regarding the head of the subject, and wherein the plotted value in the radar chart provides visualization of the brain activity of the subject in the corresponding one of the plurality of regions.

* * * * *